United States Patent [19]
Mahony et al.

[11] Patent Number: 6,045,993
[45] Date of Patent: Apr. 4, 2000

[54] METHOD, REAGENT AND KIT FOR GENOTYPING OF HUMAN PAPILLOMAVIRUS

[75] Inventors: James B Mahony, Oakville, Canada; Alan W Seadler, Export; Timothy D Kierstead, Pittsburg, both of Pa.; Sylvia Chong, Hamilton, Canada

[73] Assignee: Visible Genetics Inc., Toronto, Canada

[21] Appl. No.: 09/087,655

[22] Filed: May 30, 1998

[51] Int. Cl.[7] .............................. C12Q 1/70; C12Q 1/68; C07H 21/02; C07H 21/04

[52] U.S. Cl. ................................. 435/5; 435/6; 435/7.1; 435/21; 435/28; 536/23.1; 536/24.3; 536/24.31; 536/24.32; 536/24.33

[58] Field of Search ............................. 435/5, 6, 7.1, 21, 435/28; 536/23.1, 24.3, 24.31, 24.32, 24.33

[56] References Cited

U.S. PATENT DOCUMENTS

| | | |
|---|---|---|
| 4,849,331 | 7/1989 | Lorincz . |
| 4,849,332 | 7/1989 | Lorincz . |
| 4,849,334 | 7/1989 | Lorincz . |
| 4,908,306 | 3/1990 | Lorincz . |
| 5,364,758 | 11/1994 | Meijer et al. ................. 435/5 |
| 5,447,839 | 9/1995 | Manos et al. . |
| 5,527,898 | 6/1996 | Bauer et al. ................. 536/24.3 |

FOREIGN PATENT DOCUMENTS 0 264 659   12/1988   European Pat. Off. .

OTHER PUBLICATIONS

Visible genetics inc. Protocol Booklet, "HPV Genotyping Resolution High GeneKit", pp. 1–23, Mar. 3, 1998.

Ting, Yi and M. Michele Manos, "Detection and Typing of Genital Human Papillomaviruses", in PCR Protocols A Guide to Methods and Applications, Academic Press, Inc., pp 356–367, 1990.

Husman, et al. Analysis of Cylomorphologically Abnormal Cervical Scrapes for the Presence of 27 mucosotropic Human Papillomavirus Genotypes, using Polymerase Chain Reaction Inj. J Cancer 1994. vol. 56, pp. 802–806.

Husman, et al. The use of General Primers GP5 and GP6 elongated at their 3'J ends with adjacent highly conserved sequences improves human papillomavirus detection by PCR. Gen Virology 1995. vol. 76, pp. 1057–1062.

*Primary Examiner*—Jeffrey Fredman
*Assistant Examiner*—Arun Chakrabarti
*Attorney, Agent, or Firm*—Oppedahl & Larson LLP

[57] ABSTRACT

The sequence of human papillomavirus present in a sample is determined by amplifying a portion of the L1 open reading frame of human papillomavirus genome to form L1 amplicons containing plus and minus amplified strands using MY09 and MY11 amplification primers, and then determining the positions of at least the A bases in the antisense amplicon using a consensus sequencing primer which is shifted six bases with respect to the MY09 primer (MY09-6). This primer has the sequence ARRGGAWACT GATCWARDTC (Seq. ID No. 3)

16 Claims, No Drawings

METHOD, REAGENT AND KIT FOR GENOTYPING OF HUMAN PAPILLOMAVIRUS

This application relates to a method, reagent and kit for genotyping of human papillomavirus, and in particular to the sequencing of human papillomavirus for determination of viral type.

Cancer of the cervix is one of the most common malignancies in women around the world. Over 90% of both invasive cervical cancer lesions and precursor lesions are associated with the presence of human papillomavirus (HPV), and many epidemiological studies have established that HPV infection is the major risk factor for squamous intraepithelial lesions and cervical carcinoma. Recently, the involvement of HPV in the etiology of cervical cancer has been extended to prostate cancer. Epidemiological studies have shown that men with HPV infections in their 20's and 30's are five times more likely to develop prostate cancer in their 50's and 60's.

In view of the potential significance of HPV infection, it would clearly be of interest to be able to routinely test samples for the presence of HPV. However, of the more than 54 genetic types of HPV which have been described (an HPV sample is designated as a new "type" when it has less than 90% nucleotide homology in the E6, E& and L1 genes with previously characterized HPV types), only about 20% have been shown to be oncogenic. Thus, it is not sufficient to detect HPV. Meaningful diagnosis also requires the determination of the genetic type of any infecting virus.

U.S. Pat. No. 5,447,839, which is incorporated herein by reference, discloses a method for detection and typing of HPV. In this method, HPV DNA sequences in a sample are amplified by polymerase chain reaction (PCR) amplification using consensus primers which amplify both oncogenic and non-oncogenic HPV types. Thus, the presence of HPV in the sample is indicated by the formation of amplification products. HPV is then typed using type-specific DNA probes which hybridize with the amplified region of DNA. The type-specific hybridization probes disclosed in this patent are capable of identifying and distinguishing among five known oncogenic types of HPV, namely HPV-6, HPV-11, HPV-16, HPV-18 and HPV-33.

U.S. Pat. Nos. 4,849,331, 4,849,332, 4,849,334 and 4,908,306 which are incorporated herein by reference relate to HPV-35, HPV-43, HPV-44, and HPV-56. According to these patents, these types may be identified by hybridization with type-specific probes, although no actual sequences for such probes are disclosed.

Identification of other HPV types is discussed in Schiffman, et al. (1993). "Epidemiologic evidence showing that human papillomavirus infection causes most cervical intraepithelial neoplasia", *J. Nat'l Cancer Inst.* 85: 958–964; zur Hausen, H., (1994) "Molecular pathogenesis of cancer of the cervix and its causation by specific human papillomavirus types", *Curr. Top. Microbiol. Immunol.* 186: 131–156; and de Villiers, E. (1994). "Human pathogenic papillomavirus types: an update", *Curr. Top. Microbiol. Immunol.* 186: 1–12.

What is apparent from consideration of the art discussed above is that determination of HPV type using hybridization probes requires a substantial arsenal of distinct probes types, and a battery of tests which makes HPV typing by this approach both time consuming and expensive. Furthermore, since the number of identified types of HPV is continuing to expand, there is a need to keep developing new tests and reagents and a risk that an existing hybridization probe is in fact unable to distinguish between a known genotype and a yet-to-be characterized genotype. Thus, it would be advantageous to perform the genotyping of HPV samples using reagents that are not-type specific. It is an object of the present invention to provide such a method.

SUMMARY OF THE INVENTION

This and other objects of the invention are achieved using a method for determining the sequence of human papillomavirus present in a sample comprising the steps of:

(a) amplifying a portion of the L1 open reading frame of human papillomavirus genome to form L1 amplicons containing plus and minus amplified strands using first and second amplification primers; and (b) determining the positions of at least one species of nucleotide within at least one of the plus and minus amplified strands by extension of a sequencing primer which hybridizes with the plus or minus amplified strand in the presence of a chain-terminating nucleotide, wherein the first amplification primer has the sequence given by Seq. ID. No. 1, and the sequencing primer has the sequence given by Seq. ID No. 3. The second amplification primer preferably has the sequence given by sequence ID No. 2.

DETAILED DESCRIPTION OF THE INVENTION

The present invention provides a method for sequencing, and thus for determining the genotype of HPV that may be present in a sample. Suitable samples for use in the present invention include but are not limited to cervical swabs or scrapings, urethral swabs, vaginal/vulval swabs, urine and biopsied tissues samples.

In accordance with the present invention, a sample containing, or suspected of containing HPV is combined with a pair of amplification primers effective to amplify a portion of the L1 open reading frame of the HPV genome via polymerase chain reaction (PCR) amplification. The procedures for PCR amplification have become well known, and will not be repeated at length here. Basically, however the two primers are selected to flank a region of interest to be amplified, one primer binding to each of the strands of the DNA duplex such that template-dependent primer extension proceeds in the direction of the other primer binding site. Repeated cycles of annealing, extension and denaturation result in the production of many copies of both the plus and minus (sense and antisense) strands in the region flanked by the primers. The double stranded copies of the L1 region are referred to herein as L1 amplicons. Each such a amplicon of course contains a plus and a minus strand.

Consensus amplification primer sequences for the L1 open reading frame of HPV have been previously described in U.S. Pat. No. 5,447,839 and in Ting et al., "Detection and Typing of Genital Human Papillomaviruses", *PCR Protocols: A Guide to Methods and Applications,* Academic Press, 1990, pp. 356–367. These primers, designated as MY11 and MY09, respectively, have the following sequences:
MY11, positive strand primer: GCMCAGGGWC ATAAYAATGG Seq. ID. No. 1
MY09, negative strand primer: CGTCCMARRG GAWACTGATC Seq. ID No. 2.
A third primer, HMB01 (SEQ ID No. 4) is often used in combination with MY09 and MY11 to amplify HPV 51 which is not amplified efficiently with MY09 and MY11 alone. Hildesheim et al., *J. Infect. Dis.* 169: 235–240 (1994).

This amplification primer, or other additional primers which increase amplification efficiency for difficult types may be included in amplification mixtures when practicing the present invention. See Qu et al. (1997) *J. Clin. Microbiol.* 35: 1304–1310. In a preferred embodiment of the present invention, the MY11, MY09 and HMB01primers are used to amplify HPV that may be present in the sample to be tested. This results in the production of L1 amplicons.

The next step in the method of the invention is the determination of the nucleic acid sequence of at least the minus strand of the L1 amplicons. This is accomplished using a chain termination sequencing method and a sequencing primer having the sequence:
ARRGGAWACT GATCWARDTC Seq. ID No. 3.

Like PCR, chain termination nucleic acid sequencing is a well known procedure, although many variations have been developed. In the basic procedure for chain-termination sequencing, a polynucleotide to be sequenced is isolated, rendered single stranded if necessary, and placed into four vessels. In each vessel are the necessary components to replicate the DNA strand, i.e., a template-dependant DNA polymerase, a short primer molecule complementary to a known region of the DNA to be sequenced, and the standard deoxynucleotide triphosphates (dNTP's) commonly represented by A, C, G and T, in a buffer conducive to hybridization between the primer and the DNA to be sequenced and chain extension of the hybridized primer. In addition, each vessel contains a small quantity of one type (i.e., one species) of dideoxynucleotide triphosphate (ddNTP), e.g. dideoxyadenosine triphosphate (ddA).

In each vessel, the primer hybridizes to a specific site on the isolated DNA. The primers are then extended, one base at a time to form a new nucleic acid polymer complementary to the isolated pieces of DNA. When a dideoxynucleotide triphosphate is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

In principle, any oligonucleotide primer which binds to a target DNA sequence can be used as the sequencing primer in this process to produce sequencing fragments for analysis. In practice, however, different primers provide quite different results. Some primers produce results with a substantial amount of "background," i.e., undesirable noise or unknown signals included in the sequencing trace. Such signals may result from non-specific binding of primers to undesired regions of the sample or other unknown sources or contaminants which create undesired extension products from the amplification and sequencing steps. The undesired products may have similar lengths to the sequencing products and therefore their bands may overlap on a sequencing gel. In addition, some primers allow the sequencing of only limited portions of an amplified strand or give rise to "hard stops" in the sequencing results. Others allow sequencing of long regions of the same amplicon, without hard stops. It is difficult, if not impossible to predict which primers will perform well, and which will perform poorly.

The sequencing primer of the present invention (Seq. ID. No. 3) is the culmination of a series of experiments to identify a sequencing primer which could be used to efficiently sequence the L1 amplicon produced by the MY11/MY09 primers. It was desirable to have a primer which would sequence at least 250 to 300 bases consistently, and which was not prone to hard stops or other anomalies such as background in the sequencing fragments. The sequencing primer of the invention meets these criteria. Other primers which were evaluated do not.

We first tried using the sense (positive strand) primer MY11, labeled with Cy5.5 fluorophore for sequencing. This primer produced only poor quality sequencing results with high background and hard stops after about 100 bases. We next tried a nested primer based on MY11 called MY11-3 (shifted by three bases in the 3' direction relative to MY11). This decreased the background and improved the sequence quality, but we still observed hard stops in most of the sequencing runs. Next, we tried an antisense primer MY09 labeled with Cy5.5. This primer yielded much improved sequence without the hard stops. Sequence lengths of over 300 bases, but there was still a background with this primer. The primer of the invention, is based on MY09 namely, MY09-6 (shifted in by 6 bases in the 3' direction relative to MY09). This primer gives much better sequence without the background yielding over 300 bases called in most runs.

Because the sequencing primer of the invention hybridizes just inside the end of the plus strand of the L1 amplicon that is defined by the MY09 amplification primer, it will be appreciated that the sequence of the second primer is not critical to the invention. Thus, while the MY11 primer is preferred as the second amplification primer, other amplification primers that hybridize in a non-type-specific manner in the vicinity of the L1 region of the HPV genome can be used in combination with MY09. Examples of such primers might include variations of MY11 in which one or more bases is deleted from or added to the ends. Additional bases may be complementary to the HPV sequence or may be selected to introduce selected functionality to the amplified product. For example, a primer such as MY11 could be modified at the 5'-end of the o sequence to add a complementary sequence to the M13 primer, thus permitting M13 sequencing primer to be used for sequencing in the reverse direction.

The method of the present invention can be performed where the amplification and sequencing reactions are discrete steps in which the L1 region of the HPV genome is first amplified and then, after optional purification, the sequence of one strand is determined. In this case, it may be desirable to include a capture-label such as biotin on one of the amplification primers. This would permit capture of the duplex DNA product after the final amplification cycle on an avidin or streptavidin coated support (for example avidin-coated magnetic beads), and washing to remove the amplification reagents such as including unreacted primer. One strand of the DNA would then be eluted from the support to provide either a solution with the strand to be sequenced or a support with the strand to be sequenced immobilized thereon ready for sequencing.

Sequencing of the amplicon can be done using conventional sequencing in which one cycle of primer annealing, extension and denaturation are performed. Sequencing may also be done using a multiple cycle sequencing technique such a "cycle sequencing." As described by Kretz et al. in *PCR Methods and Applications,* Cold Spring Harbor Laboratory Press 1994, pp. S107–S11, cycle sequencing involves combining a sequencing primer with a template and processing the template through multiple cycles (e.g., about 30 cycles) of thermal conditions adapted for denaturation, primer annealing and primer extension using a thermostable polymerase enzyme such as Taq polymerase.

As an alternative to the performance of the amplification and sequencing reactions as discrete steps, a combined process of the type described generally by Ruano in U.S. Pat. No. 5,427,911 which is incorporated herein by reference. In this method, some number of initial amplification cycles (e.g, 15–20) are performed using the amplification primer pair, including at least primer MY09 (Seq. ID No. 2). Then, the sequencing primer of the invention (Seq. ID No. 2) and a chain-terminating nucleotide triphosphate are added to the amplification mixture and some number of additional cycles (e.g., 15–20) to produce sequencing fragments for analysis.

The method of the invention may be used to explicitly determine the positions of all four species of nucleotide triphosphates by carrying out sequencing reactions in which chain-terminating nucleotides corresponding to each of the four types of bases are used. As explained in U.S. Pat. application Ser. No. 08/577,858 and International Patent Publication No. WO 97/20202, which are incorporated herein by reference, however, the explicit determination of all of the bases is not always necessary for genotyping virus with known sequences. In the case of HPV, determination of the positions of the A bases within the L1 region allows genotyping of all known oncogenic genotypes.

In order to detect the sequencing fragments, it is generally necessary to incorporate a detectable label into the fragments. Such labels can be, for example, radiolabels, chromophores or chromogenic labels, or fluorescent or fluorogenic labels. Preferred labels are fluorescent labels suitable for detection in existing DNA sequencing instrumentation, including fluorescein, Texas Red X, carboxy-X-rhodamine, carboxyfluorescein, carboxytetramethyl-rhodamine, carboxycyanine 5.0 (Cy5.0), and carboxycyanine 5.5 (Cy5.5).

The detectable label is preferably affixed to the sequencing primer of the invention (Seq. ID No. 3). Labels may also be affixed to the chain terminating nucleotide triphosphate or to bases which will be incorporated in the extending chain.

The invention will now be further described through the following non-limiting examples.

EXAMPLE 1

DNA was prepared from cervical specimens (swabs or brushings) as described by Mahony et al. (*J. Clin. Microbiol.* 30:2241–2245,1992). Swabs are placed into in 0.2 ml ddH2O containing 1% Tween 20 detergent. Proteinase K is added to a final concentration of 200 ug/ml and the sample incubated for 1 hr at 55° C. or 18 hr at room temperature. Incubate further at 95° C. for 10 min. Extract the DNA from 0.2 ml of sample using XTRAX™ DNA Extraction Kit (Gull Laboratories, St. Lake City) and resuspend DNA in 20 ul ddH2O. A lysis solution control can be made by adding 0.2 ml Proteinase K/Tween 20 to a sterile tube and treating the tube like the others.

PCR amplification is performed for 10 reactions as follows. Take a sterile 1.5 ml microfuge tube and prepare enough Master Mix for 10 reactions as follows. Add 100 ul 10× PCR buffer without MgCl$_2$ (Perkin-Elmer); 160 ul of 25 mM MgCl$_2$ 16 ul of a mixture of four dNTPs at 200 uM each, 2.5 ul of primer MY09 at 200 uM, 2.5 ul of primer MY11 at 200 uM, 1.25 ul of primer HMB01 at 40 uM, 612.75 ul ddH2O, and 5 ul TaqGold DNA polymerase (Perkin-Elmer) at 5 Units/ul.

The following primers are present:

5'-GCM CAG GGW CAT AAY AAT GG -3' SEQ ID No. 1

5'-CGT CCM ARR GGA WAC TGA TC -3' SEQ ID No. 2

5'-GCG ACC CAA TGC AAA TTG GT -3' SEQ ID No. 4

Prepare PCR reaction tubes (0.2 ml tubes, thin walls), label and set them in the rack. (If not using a heated lid thermocycler, add one drop of mineral oil to each PCR tube). When ready to put the reaction mix into the PCR tubes, add TaqGold DNA polymerase last. Mix well and use mix as soon as possible. Put 90 ul of the Master Mix solution prepared above into each PCR tube. Add 10 ul of sample DNA to each tube. Include the following controls: One negative control per 5 samples. This negative control contains 10 ul of water instead of 10 ul of sample. One lysis solution control: add 10 ul of the lysis solution to make sure that the lysis solution was not contaminated. Close each tube as soon as the sample has been added. Alternate negative controls with samples: one negative control per 5 samples. When all the samples have been added, put the tube in a the thermal cycler that can take thin walled tubes (M J Research PTC200).

Thermal cycles proceed as follows:

94° C./10 min then 35 cycles of the following:

94° C./15 sec

55° C./15 sec

72° C./70 sec after these cycles, then continue with

72° C./5 min

4° C./until ready to load.

Determine the concentration of PCR product as follows. Mix 8 ul of the PCR reaction mix with 2 ul loading buffer and load the entire 10 ul on a 2% agarose gel using standard conditions. In a parallel lane electrophorese 8 ul of Mass ladder (Gibco low DNA mass ladder cat. No. 10068-013) plus 2 ul loading buffer. Determine the amount of DNA present in the sample by matching the PCR product band intensity with a similar intensity in the mass ladder. Calculate the concentration of amplicon as follows: if the sample has a band intensity between the intensities for the 200 and 400 bp bands then the DNA concentration would be ~60 ng/8 ul or 7.5 ng/ul.

Purify the PCR amplified product using a QIAquick column (QIAGEN Inc.) according to the manufacturer's instructions. The entire 100 ul PCR reaction is added to the column and eluted in 30 ul of ddH2O. The DNA will be concentrated approximately 3-fold at this stage. For the example above, the DNA concentration will be 3×7.5 ng/ul= 22.5 ng/ul.

The minimal DNA concentration required for sequencing is 8 ng/ul and the maximum is 60 ng/ul. Dilute the purified DNA so the concentration is 8–60 ng/ul. (If the DNA concentration is below 8 ng/ul then re-amplify the original sample using more of the sample).

Set up the following four PCR cycle sequencing reactions for each sample. For each sample label four tubes as follows: A, C, G, T. In another tube prepare 14 ul of Master Mix by combining the following: 2 ul Sequencing buffer, 2 ul 25 mM MgCl$_2$, 2 ul Cy 5.5-labeled reverse sequencing primer MY09-6 (5'-CGT CCM ARR GGA WAC TGA TC -3', Seq ID No 2) at a concentration of 1.5 pmol/ul, 2 ul THERMOSEQUENASE polymerase diluted 1:8 in enzyme dilution buffer (Amersham PLC.), 2 ul ddH2O and 6 ul purified sample DNA. To each of the four tubes labeled A, C, G, T add 3 ul of the respective dideoxynucleotide triphosphate (ddATP, ddCTP, ddGTP, or ddTTP) and 3 ul of the Master Mix. When all the samples have been added, put the tube in the thermal cycler Thermal cycles proceed as follows:
94° C./2 min
then 35 cycles of the following:
94° C./40 sec
55° C./20 sec
70° C./120 sec
after these cycles, then continue with
70° C./2 min
4° C./until ready to load.

Take 1 ul of the sequencing reaction and add it to 1 ul of the MICROGENE BLASTER loading buffer. Store the rest of the reaction at −20° C. Immediately before loading, heat the sample/loading buffer to 94° C. for 1.5 min. Cool rapidly on ice and load 2 ul on a single lane of the MICROGENE BLASTER DNA sequencer (Visible Genetics Inc, Toronto, Canada) at 1300 V (54° C.) for 40 min.

EXAMPLE 2

DNA was prepared from cervical specimens (swabs or brushings) as described by Mahony et al. (*J. Clin. Microbiol.* 30:2241–2245,1992). Swabs are placed into in 0.2 ml ddH2O containing 1% Tween 20 detergent. Proteinase K is added to a final concentration of 200 ug/ml and the sample incubated for 1 hr at 55° C. or 18 hr at room temperature. Incubate further at 95° C. for 10 min. Extract the DNA from 0.2 ml of sample using XTRAXTM DNA Extraction Kit (Gull Laboratories, St. Lake City) and resuspend DNA in 20 ul ddH2O. A lysis solution control can be made by adding 0.2 ml Proteinase K/Tween 20 to a sterile tube and treating the tube like the others.

PCR amplification is performed for 10 reactions as follows. Take a sterile 1.5 ml microfuge tube and prepare enough Master Mix for 10 reactions as follows. Add 100 ul 10× PCR buffer without $MgCl_2$ (Perkin-Elmer); 160 ul of 25 mM $MgCl_2$, 16 ul of a mixture of four dNTPs at 200 uM each, 2.5 ul of primer MY09 at 200 uM, 2.5 ul of primer MY11 at 200 uM, 1.25 ul of primer HMB01 at 40 uM, 612.75 ul ddH2O, and 5 ul TaqGold DNA polymerase (Perkin-Elmer) at 5 Units/ul.

The following primers are present:

5'-GCM CAG GGW CAT AAY AAT GG -3' SEQ ID No. 1

5'-CGT CCM ARR GGA WAC TGA TC -3' SEQ ID No. 2

5'-GCG ACC CAA TGC AAA TTG GT -3' SEQ ID No. 4

Prepare PCR reaction tubes (0.2 ml tubes, thin walls), label and set them in the rack. (If not using a heated lid thermocycler, add one drop of mineral oil to each PCR tube). When ready to put the reaction mix into the PCR tubes, add TaqGold DNA polymerase last. Mix well and use mix as soon as possible. Put 90 ul of the Master Mix solution prepared above into each PCR tube. Add 10 ul of sample DNA to each tube. Include the following controls: One negative control per 5 samples. This negative control contains 10 ul of water instead of 10 ul of sample. One lysis solution control: add 10 ul of the lysis solution to make sure that the lysis solution was not contaminated. Close each tube as soon as the sample has been added. Alternate negative controls with samples: one negative control per 5 samples. When all the samples have been added, put the tube in a the thermal cycler that can take thin walled tubes (M J Research PTC200).

Thermal cycles proceed as follows:
94° C./10 min
then 35 cycles of the following:
94° C./15 sec
55° C./15 sec
72° C./70 sec
after these cycles, then continue with
72° C./5 min
4° C./ until ready to load.

Determine the concentration of PCR product as follows. Mix 8 ul of the PCR reaction mix with 2 ul loading buffer and load the entire 10 ul on a 2% agarose gel using standard conditions. In a parallel lane electrophorese 8 ul of Mass ladder (Gibco low DNA mass ladder cat. No. 10068-013) plus 2 ul loading buffer. Determine the amount of DNA present in the sample by matching the PCR product band intensity with a similar intensity in the mass ladder. Calculate the concentration of amplicon as follows: if the sample has a band intensity between the intensities for the 200 and 400 bp bands then the DNA concentration would be 60 ng/8 ul or 7.5 ng/ul.

Purify the PCR amplified product using a QIAquick column (QIAGEN Inc.) according to the manufacturer's instructions. The entire 100 ul PCR reaction is added to the column and eluted in 30 ul of ddH2O. The DNA will be concentrated approximately 3-fold at this stage. For the example above, the DNA concentration will be 3×7.5 ng/ul= 22.5 ng/ul.

The minimal DNA concentration required for sequencing is 8 ng/ul and the maximum is 60 ng/ul. Dilute the purified DNA so the concentration is 8–60 ng/ul. (If the DNA concentration is below 8 ng/ul then re-amplify the original sample using more of the sample).

Set up a single "A" base PCR cycle sequencing reaction for each sample. In a microfuge tube prepare Sequencing Master Mix for 10 reactions by combining the following: 10 ul Sequencing buffer, 10 ul 25 mM $MgCl_2$, 10 ul Cy 5.5-labeled reverse sequencing primer MY09-6 containing (1.5 pmol/ul), 10 ul THERMOSEQUENASE polymerase diluted 1:8. To each of ten tubes add 4 ul of the sequencing Master Mix and 3 ul of sample DNA. Mix be pipetting.

In a separate tube add 3 ul of each sample (in sequencing master mix buffer) to 3 ul of dideoxyadenosine triphosphate (ddATP) terminator. When all the samples have been added, put the tubes in the thermal cycler. Thermal cycles proceed as follows:
94°/2 min
then 35 cycles of the following:
94°/40 sec
55° C./20 sec
70° C./120 sec
after these cycles, then continue with
70° C./2 min
4° C./until ready to load.

Take 1 ul of the sequencing reaction and add it to 1 ul of the MICROGENE BLASTER loading buffer. Store the rest of the reaction at −20° C. Immediately before loading, heat the sample/loading buffer to 94° C. for 1.5 min. Cool rapidly on ice and load 2 ul on a single lane of the MICROGENE BLASTER DNA sequencer at 1300 V (54° C.) for 40 min.

EXAMPLE 3

If using specimens collected CYTYC PRESERVCYT solution, mix sample thoroughly by vortexing, stirring or shaking. Transfer 1000 ul of the sample to a microcentrifuge tube and pellet the cellular material by centrifugation for 1 minute at 16,000×g. Aspirate the supernatant, and add XTRAX™ DNA extraction buffer (1000 ul) to each sample and mix by gently swirling. Vortex thoroughly to break up any clumps. Centrifuge for 5 sec. at 16,000×g. Transfer 700 ul of supernatant to a Sarstedt 2.0 ml screw cap microtube with attached cap. Microwave the tube on high (775 Watts) for 10 sec. The Extraction Buffer should turn from clear to opaque when heated and the tube should be warm to ensure proper microwave treatment. Gently mix the contents of the tube and microwave on high (775 watts) for 3 more seconds). Cooling the tube at this stage for 3 minutes at room temperature or 1 minute on ice may facilitate precipitation of undesired materials during centrifugation.

The tube is then centrifuged for 1 minute to pellet precipitated protein. Without disturbing the pellet, transfer 500 ul of supernatant to a new micro tube capable of holding 1.5 ml. Add 500 ul of molecular grade isopropanol to each tube. The final volume should be 1000 ul. Mix the contents of the tube thoroughly by vortexing or inversion and incubate at −70° C. for 15 minutes. Centrifuge for 1 minute to pellet DNA. Decant or aspirate the supernatant without disturbing the DNA pellet, and then add 1000 ul of 70% ethanol to wash the pellet. Vortex thoroughly and centrifuge again to recover a washed DNA pellet. Remove all supernatant by aspiration or decanting. Add 35 ul of TE buffer to dissolve the DNA pellet and vortex.

For amplification, combine 5 ul of sample with 39.75 ul ddH$_2$O, 5.0 ul 10×PCR master mix (10×PCR master mix contains: 10 uM MY09, 10 uM MY11, 0.6 uM REV HPV51 primer, 4.0 mM each dATP, dCTP, dGTP and dTTP, 25 mM MgCl$_2$, 100 mM Tris, pH 8.3 and 500 mM KCl) and 0.25 ul PCR Taq Polymerase (5 U/ul) in a 0.2 ml thin-walled amplification tube. Place the sample into a thermocycler and process as follows:

| | | |
|---|---|---|
| Denaturation | 95° C. | 10 minutes |
| then 40 cycles of | | |
| Denaturation | 94° C. | 30 seconds |
| Annealing | 55° C. | 30 seconds |
| Extension | 72° C. | 75 seconds |
| then finish with | | |
| Extension | 72° C. | 8 minutes |
| hold at 4° C. until ready for use. | | |

An aliquot of the amplified material is analyzed by agarose gel electrophoresis to determine the approximate concentration of the L1 amplicon produced. An amount of sample containing 6–480 ng of L1 amplicon is used in the sequencing reaction.

To sequence the L1 amplicon, pipette 3.0 ul of each sequencing termination mixture into labeled individual 0.2 ml thin-walled amplification tubes and place on ice. Each sequencing termination mixture is 750 uM of each of the four dNTP's plus 5.0 uM of the appropriate dideoxynucleotide triphosphate (ddNTP). Then prepare the following mixture in a microcentrifuge tube: 1.40 ul 10×Sequencing Mix (contains 107.5 mM dithiothreitol, 400 mM Tris, pH 9.0, 73.0 mM MgCl$_2$ and 8.4 uM CY5.5-labeled MY-09 sequencing primer); 1.0 ul sequencing Taq (TAQ-FS™, 9 U/ul). Adjust the final volume to 14.00 ul with ddH$_2$O and then pipette 3.0 ul of the mixture into each of the four sequencing termination reaction tubes. The tubes are then placed in a thermocylcer and processed as follows:

| | | |
|---|---|---|
| Denaturation | 94° C. | 2 minutes |
| then 35 cycles of | | |
| Denaturation | 94° C. | 40 seconds |
| Annealing | 55° C. | 20 seconds |
| Extension | 70° C. | 2 minutes |
| then finish with | | |
| Extension | 70° C. | 2 minutes |

Add 6 ul of stop loading dye and store a 4° C. until ready for loading onto an electrophoresis gel for sequence analysis.

What is claimed is:

1. A method for determining the genotype of a human papillomavirus present in a sample comprising the steps of:
   (a) amplifying a portion of the L1 open reading frame of human papillomavirus genome to form L1 amplicons containing plus and minus amplified strands using first and second amplification primers; and
   (b) determining the positions of at least one species of nucleotide within at least one of the plus and minus amplified strands by extension of a sequencing primer which hybridizes with the plus or minus amplified strand in the presence of a chain-terminating nucleotide, wherein the first amplification primer has the sequence given by Seq. ID. No. 2, and the sequencing primer has the sequence given by Seq. ID No. 3.

2. The method according to claim 1, wherein the second amplification primer has the sequence given by Seq. ID No. 1.

3. The method according to claim 2, wherein only the positions of the A bases are determined in step (b).

4. The method according to claim 1, wherein only the positions of the A bases are determined in step (b).

5. The method according to claim 1, wherein the amplification is performed using an amplification primer having the sequence given by SEQ ID. No 4.

6. The method according to claim 5, wherein only the positions of the A bases are determined in step (b).

7. A 20 base polynucleotide having the sequence ARRGGAWACTGATCWARDTC (Seq ID No. 3).

8. The polynucleotide according to claim 7, having a detectable label affixed thereto.

9. The polynucleotide according to claim 8, wherein the detectable label is a fluorescent label.

10. A kit for determining the sequence of human papillomavirus comprising, in packaged combination:
    (a) first and second amplification primers for amplifying a portion of the L1 open reading frame of human papillomavirus genome to form an L1 amplicon containing plus and minus amplified strands; and
    (b) a sequencing primer which hybridizes with the plus or minus amplified strand in the presence of a chain-terminating nucleotide for determining the positions of at least one species of nucleotide sequence within at least one of the plus and minus amplified strands by extension of the sequencing primer, wherein the first amplification primer has the sequence given by Seq. ID. No. 2, and the sequencing primer has the sequence given by Seq. ID No. 3.

11. The kit according to claim 10, wherein the second amplification primer has the sequence given by Seq. ID No. 1.

12. The kit according to claim 11, further comprising a third amplification primer having the sequence given by SEQ ID No. 4.

13. The kit according to claim 10, wherein the sequencing primer has a detectable label affixed thereto.

14. The kit according to claim 13, wherein the detectable label is a fluorescent label.

15. The kit according to claim 13, wherein the second amplification primer has the sequence given by Seq. ID No. 1.

16. The kit according to claim 15, further comprising a third amplification primer having the sequence given by SEQ ID No. 4.

* * * * *

UNITED STATES PATENT AND TRADEMARK OFFICE
CERTIFICATE OF CORRECTION

PATENT NO : 6,045,993
DATED : April 4, 2000
INVENTOR(S): Mahony et al.

It is certified that error appears in the above-identified patent and that said Letters Patent is hereby corrected as shown below:

Cancel claims 1-6, which were included in this Patent as a result of a Patent Office error. Claims 1-6 are the subject of a divisional application.

Signed and Sealed this

Twenty-sixth Day of December, 2000

Attest:

Q. TODD DICKINSON

Attesting Officer

Director of Patents and Trademarks

SEQUENCE LISTING

<160> NUMBER OF SEQ ID NOS: 4

<210> SEQ ID NO 1
<211> LENGTH: 20
<212> TYPE: DNA
<213> ORGANISM: Human papillomavirus
<220> FEATURE:
<223> OTHER INFORMATION: MY11 positive strand primer

<400> SEQUENCE: 1
gcmcagggwc ataayaatgg                                              20

<210> SEQ ID NO 2
<211> LENGTH: 20
<212> TYPE: DNA
<213> ORGANISM: Human papillomavirus
<220> FEATURE:
<223> OTHER INFORMATION: My09 negative strand primer

<400> SEQUENCE: 2
cgtccmarrg gawactgatc                                              20

-continued

```
<210> SEQ ID NO 3
<211> LENGTH: 20
<212> TYPE: DNA
<213> ORGANISM: Human papillomavirus
<220> FEATURE:
<223> OTHER INFORMATION: HPV sequencing primer

<400> SEQUENCE: 3
arrggawact gatcwardtc                                            20

<210> SEQ ID NO 4
<211> LENGTH: 20
<212> TYPE: DNA
<213> ORGANISM: Human papillomavirus
<220> FEATURE:
<223> OTHER INFORMATION: HPV PCR primer

<400> SEQUENCE: 4
gcgacccaat gcaaattggt                                            20
```